US008412349B2

(12) United States Patent
Barker (10) Patent No.: US 8,412,349 B2
(45) Date of Patent: Apr. 2, 2013

(54) THREE-PIECE BUTTON ANCHOR AND METHODS AND DEVICES USING THE ANCHOR

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 560 days.

(21) Appl. No.: 12/478,091

(22) Filed: Jun. 4, 2009

(65) Prior Publication Data
US 2010/0312319 A1    Dec. 9, 2010

(51) Int. Cl.
*A61N 1/04*    (2006.01)
*A61N 1/375*    (2006.01)

(52) U.S. Cl. ........... 607/116; 607/117; 607/118; 607/36
(58) Field of Classification Search .......... 607/116–118, 607/36
See application file for complete search history.

(56) References Cited

U.S. PATENT DOCUMENTS

| | | | |
|---|---|---|---|
| 4,276,882 A * | 7/1981 | Dickhudt et al. ................. | 607/9 |
| 4,414,986 A | 11/1983 | Dickhudt et al. | |
| 4,419,819 A * | 12/1983 | Dickhudt et al. ................. | 29/857 |
| 4,424,818 A * | 1/1984 | Doring et al. ................. | 607/130 |
| 5,036,862 A | 8/1991 | Pohndorf | |
| 5,464,446 A | 11/1995 | Dreessen et al. | |
| 5,628,780 A * | 5/1997 | Helland et al. ................. | 607/126 |
| 5,843,146 A * | 12/1998 | Cross, Jr. ................. | 607/115 |
| 6,181,969 B1 | 1/2001 | Gord | |
| 6,473,654 B1 | 10/2002 | Chinn | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,972,003 B2 * | 12/2005 | Bierman et al. ............... | 604/180 |
| 7,069,083 B2 | 6/2006 | Finch et al. | |
| 7,082,336 B2 * | 7/2006 | Ransbury et al. ............. | 607/126 |
| 7,499,755 B2 * | 3/2009 | Cross, Jr. ..................... | 607/117 |

(Continued)

FOREIGN PATENT DOCUMENTS

| | | |
|---|---|---|
| EP | 85417 | 8/1983 |
| EP | 988080 | 3/2000 |

(Continued)

OTHER PUBLICATIONS

U.S. Appl. No. 11/238,240, filed Sep. 29, 2005.

*Primary Examiner* — Joseph Stoklosa
(74) *Attorney, Agent, or Firm* — Frommer Lawrence & Haug LLP; Bruce E. Black (57) ABSTRACT

A lead anchor comprises a housing, and a plunger. The housing comprises a rigid body and a flexible covering disposed over at least a portion of the rigid body. The housing defines a first opening and a second opening configured and arranged to receive a lead. The housing further defines a transverse lumen. The rigid body comprises one or more projecting locking ridges extending into the transverse lumen. A plunger comprising one or more locking detents disposed thereon is configured and arranged for insertion into the transverse lumen and engaging a lead and locking with the housing by engagement of at least one of the one or more locking ridges of the housing with at least one of the one or more locking detents of the plunger. At least one suture element is formed by the flexible covering for receiving a suture to suture the lead anchor to patient tissue.

20 Claims, 11 Drawing Sheets

U.S. PATENT DOCUMENTS

| | | | |
|---|---|---|---|
| 7,529,589 B2 | 5/2009 | Williams et al. | |
| 7,787,960 B2 * | 8/2010 | Lubenow et al. | 607/116 |
| 2003/0114905 A1 | 6/2003 | Kuzma | |
| 2004/0059392 A1 | 3/2004 | Parramon et al. | |
| 2004/0116977 A1 | 6/2004 | Finch et al. | |
| 2004/0249417 A1 | 12/2004 | Ransbury et al. | |
| 2004/0249431 A1 | 12/2004 | Ransbury et al. | |
| 2005/0043765 A1 | 2/2005 | Williams et al. | |
| 2005/0165465 A1 | 7/2005 | Pianca et al. | |
| 2005/0182470 A1 * | 8/2005 | Cross, Jr. | 607/117 |
| 2005/0192594 A1 * | 9/2005 | Skakoon et al. | 606/129 |
| 2005/0228471 A1 | 10/2005 | Williams et al. | |
| 2005/0234431 A1 | 10/2005 | Williams et al. | |
| 2006/0127158 A1 | 6/2006 | Olson et al. | |
| 2006/0224225 A1 | 10/2006 | Ransbury et al. | |
| 2006/0241716 A1 | 10/2006 | Finch et al. | |
| 2007/0050005 A1 | 3/2007 | Lauro | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |
| 2007/0255379 A1 | 11/2007 | Williams et al. | |
| 2008/0077219 A1 | 3/2008 | Williams et al. | |
| 2008/0183253 A1 | 7/2008 | Bly | |
| 2008/0243220 A1 | 10/2008 | Barker | |
| 2009/0048583 A1 | 2/2009 | Williams et al. | |

FOREIGN PATENT DOCUMENTS

| | | |
|---|---|---|
| WO | WO-98/48880 A1 | 11/1998 |
| WO | WO-2004/054655 A1 | 7/2004 |
| WO | WO-2005/000398 A2 | 1/2005 |
| WO | WO-2005/077450 A2 | 8/2005 |
| WO | WO-2007/092330 A1 | 8/2007 |
| WO | WO-2008/094789 A1 | 8/2008 |
| WO | WO-2008/121708 A2 | 10/2008 |

* cited by examiner

THREE-PIECE BUTTON ANCHOR AND METHODS AND DEVICES USING THE ANCHOR

FIELD

The present invention is directed to the area of implantable electrical stimulation systems and methods of making and using the systems. The present invention is also directed to implantable electrical stimulation leads having a lead anchor as well as methods of making and using the leads, lead anchors, and electrical stimulation systems.

BACKGROUND

Spinal cord stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

Many conventional lead anchors possess inadequate lead retention strength when the lead is subjected to tensile loading. This may cause the lead to migrate proximally from the desired neurostimulation site. According to recent studies, lead migration occurs in approximately 13% of cases. Additional studies suggest that electrode migration may be the most common reason for failure to maintain long-term pain control with spinal cord stimulation. One possible cause is that anchors that rely on sutures alone vary in retention strength upon the suturing technique of the physician. Other problems associated with lead migration include lead breakage, and loose connection.

Another problem commonly associated with conventional lead anchors is patient discomfort. Many conventional lead anchors are unnecessarily bulky and awkward to carry. Other lead anchors that are not large are uncomfortable because they have jagged or sharp edges. Because spinal cord stimulators are generally worn for prolonged durations of time, patient comfort with respect to the lead anchor is important.

BRIEF SUMMARY

In some embodiments, a lead anchor comprises a housing, and a plunger. The housing comprises a rigid body and a flexible covering disposed over at least a portion of the rigid body. The housing defines a first opening and a second opening configured and arranged to receive a lead. The housing further defines a transverse lumen. The rigid body comprises one or more projecting locking ridges extending into the transverse lumen. A plunger comprising one or more locking detents disposed thereon is configured and arranged for insertion into the transverse lumen and engaging a lead disposed through the first and second openings of the housing and is configured and arranged for locking with the housing by engagement of at least one of the one or more locking ridges of the housing with at least one of the one or more locking detents of the plunger. At least one suture element is formed by the flexible covering and is configured and arranged for receiving a suture to suture the lead anchor to patient tissue.

In some embodiments, a method of implanting an implantable stimulation device comprises implanting a portion of a lead having an electrode array near tissue to be stimulated. A distal end of the lead is secured through a lead anchor. The lead anchor comprises a housing comprising a rigid body and a flexible covering disposed over at least a portion of the rigid body. The housing defines a first opening and a second opening configured and arranged to receive a lead. The housing further defines a transverse lumen. The rigid body comprises one or more projecting locking ridges. A plunger comprising one or more locking detents is disposed thereon. The plunger is configured and arranged for insertion into the transverse lumen and engaging a lead disposed through the first and second openings of the housing. The plunger is configured and arranged for locking with the housing by engagement of at least one of the one or more locking ridges of the housing with at least one of the one or more locking detents of the plunger. At least one suture element is formed by the flexible covering and is configured and arranged for receiving a suture to suture the lead anchor to patient tissue. The lead anchor is secured to the surrounding tissue using sutures.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4B is a schematic bottom view of the plunger of FIG. 4A, according to the invention;

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the invention is directed to lead anchors for implantable spinal cord stimulators, as well as the stimulators themselves and methods of use and manufacture of the lead anchors and spinal cord stimulators.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent applications Ser. Nos. 10/353,101, 10/503,281, 11/238,240; 11/319,291; 11/327,880; 11/375,638; 11/393,991; and 11/396,309, all of which are incorporated by reference.

Figure 1:
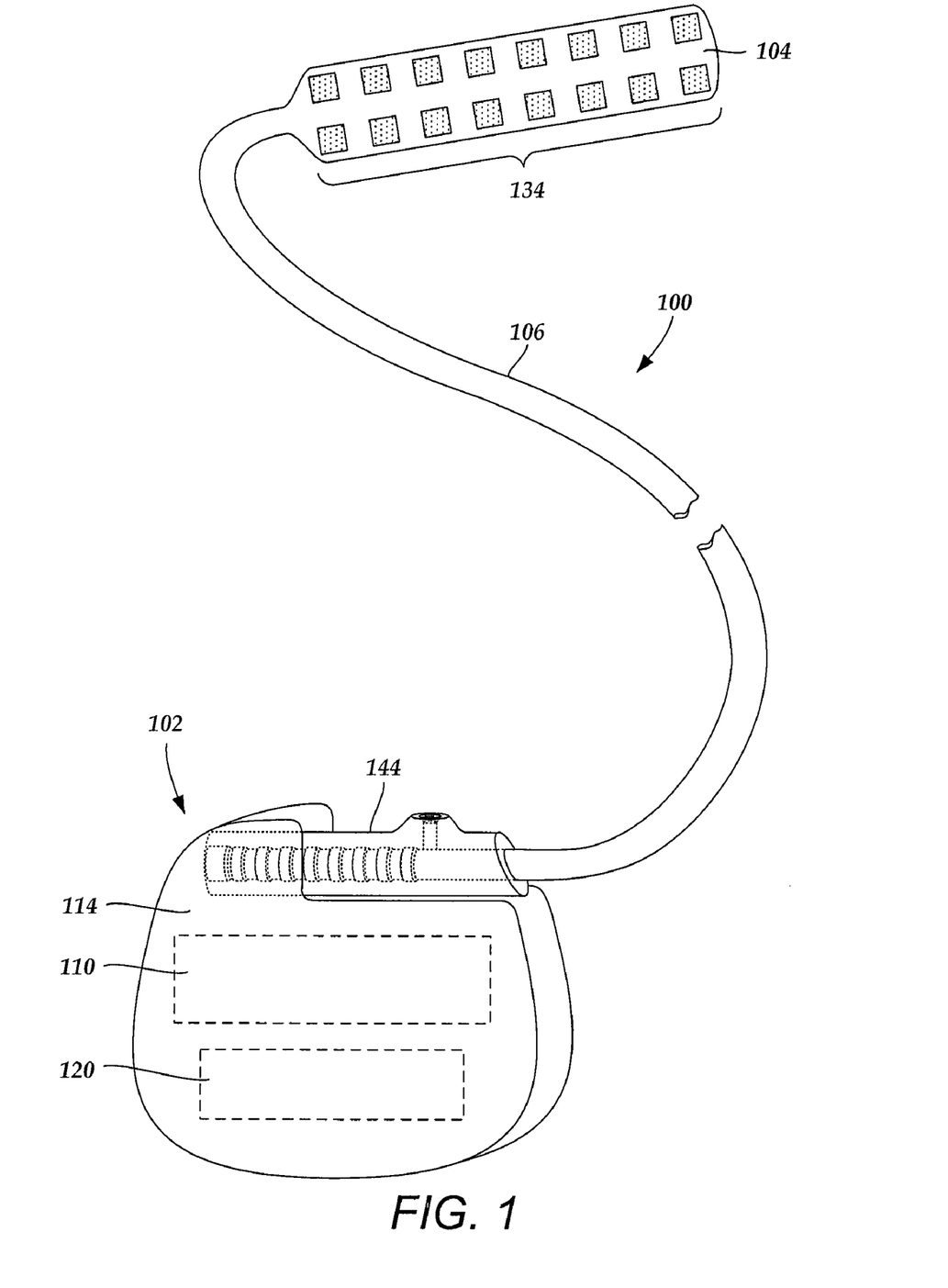
FIG. 1 is a schematic view of one embodiment of an electrical stimulation system, according to the invention.
Figure 2:
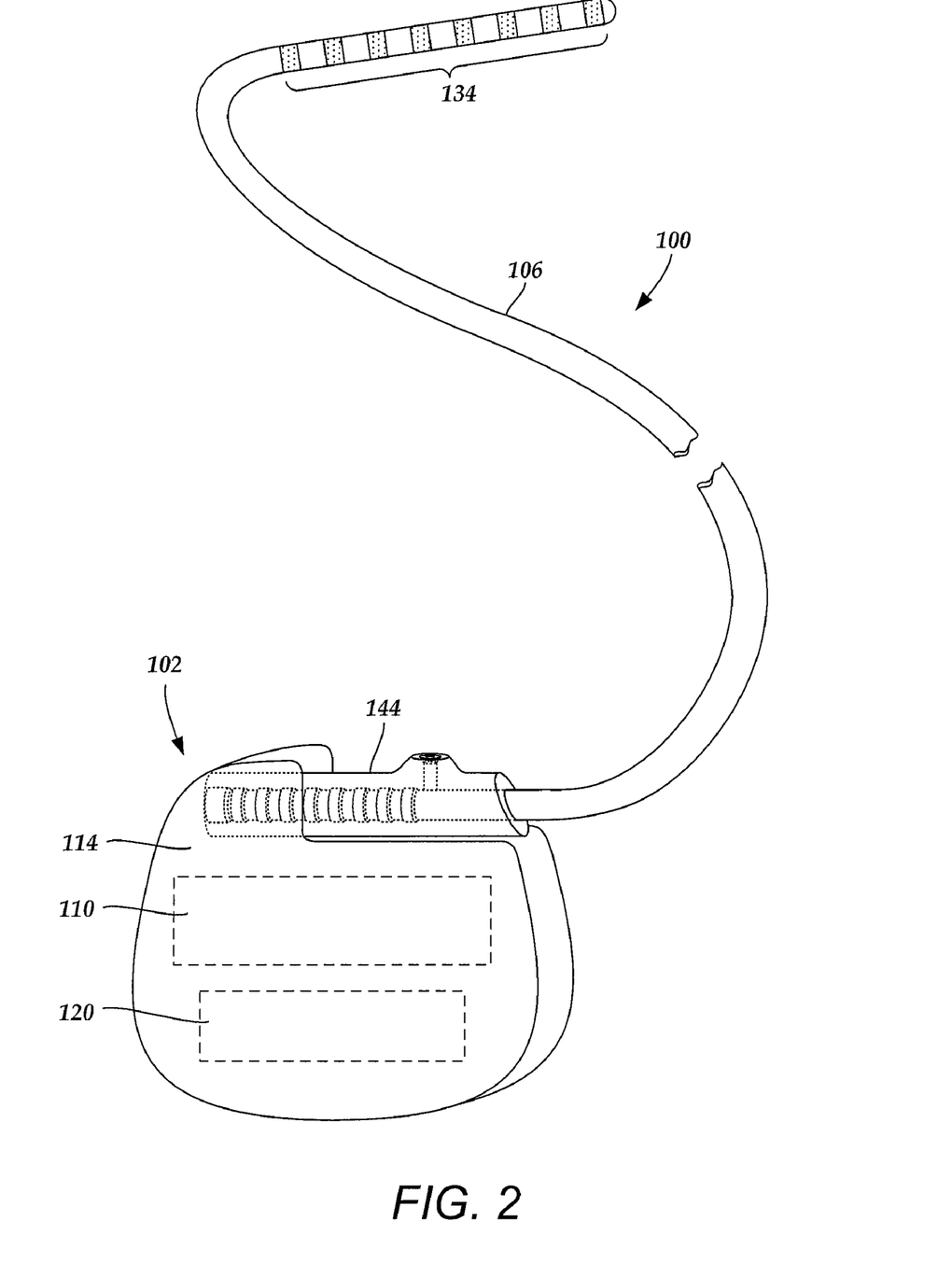
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIG. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
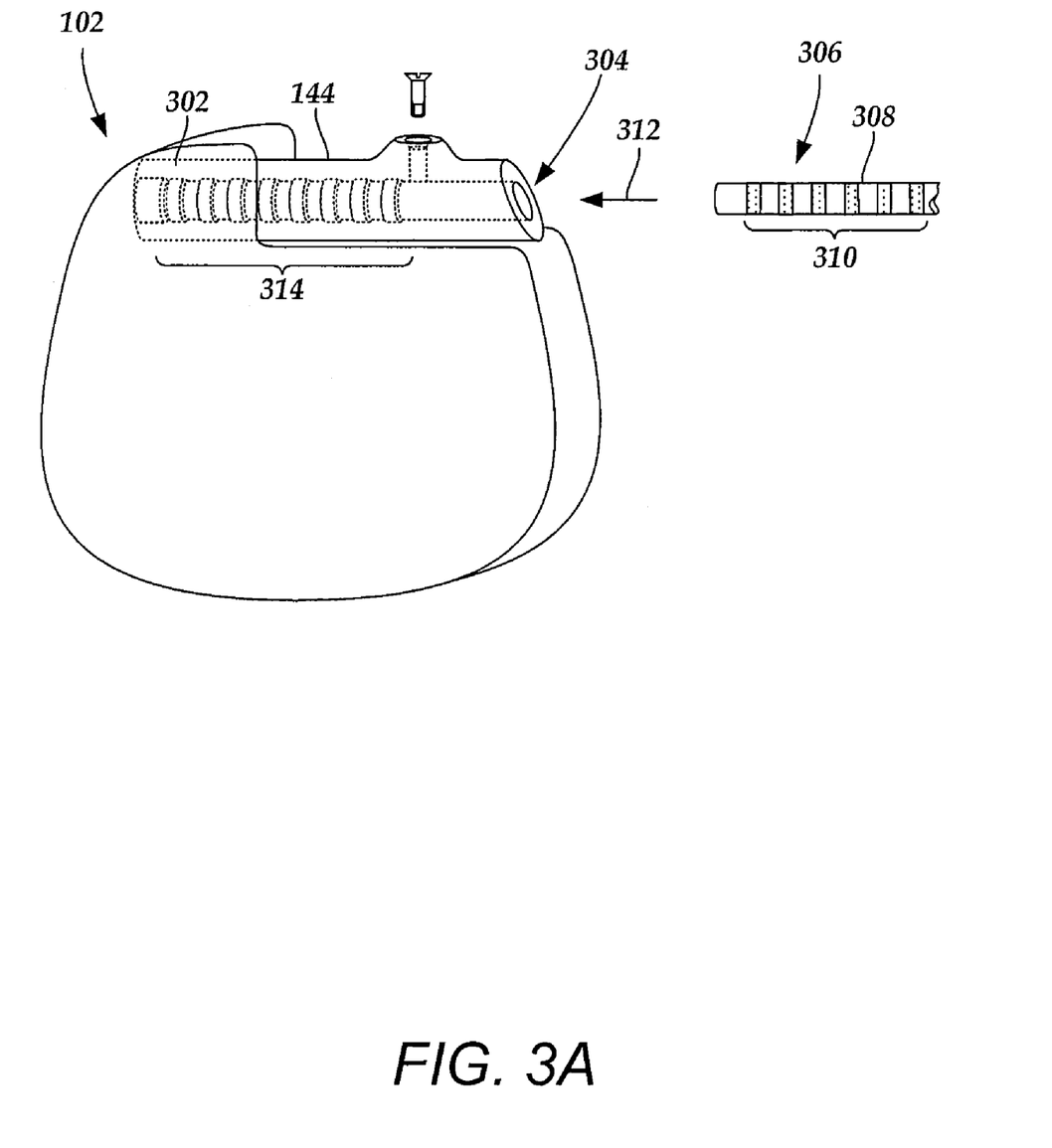
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
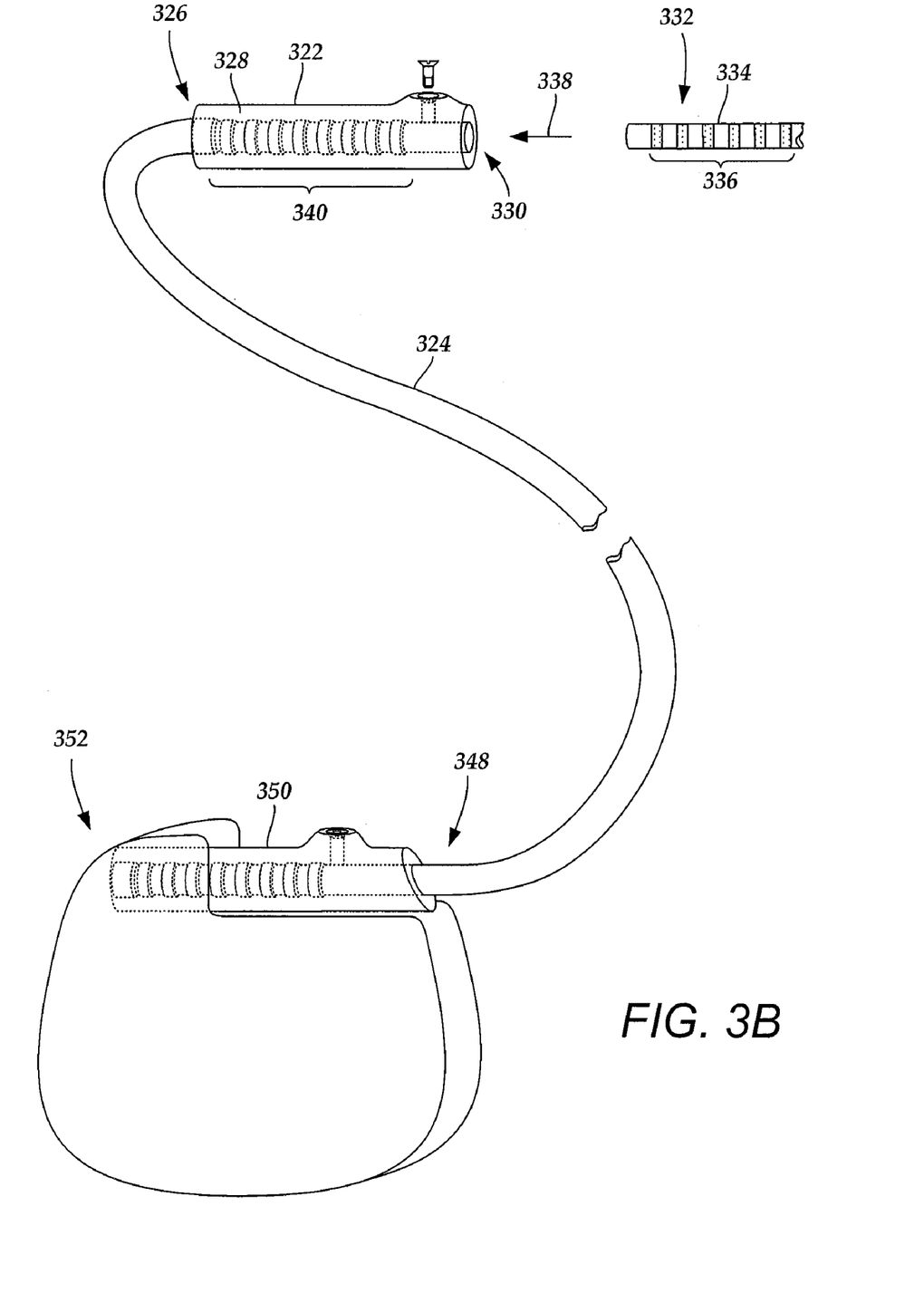
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

A lead anchor can be used in an implantable device, such as an implantable spinal cord stimulator, to anchor a lead connecting a control module to an electrode array. The plunger engages a portion of a lead disposed in the rigid body to hold the lead in the anchor. In some embodiments, the lead anchor includes a plunger, an optional flexible covering, and a rigid body that receives the plunger. In at least some embodiments, the flexible covering and the rigid body together form a housing that when coupled to the plunger locks a lead in place.

Figure 4A:
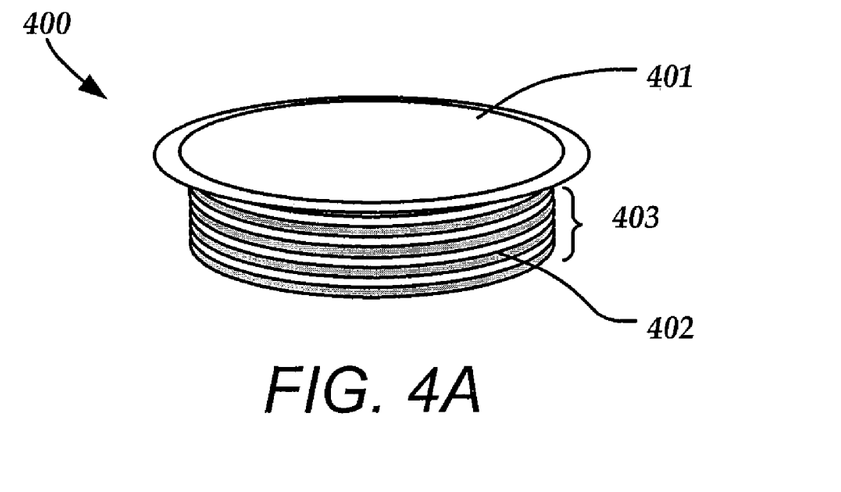
FIG. 4A is a schematic top view of one embodiment of a plunger, according to the invention.

FIGS. 4A and 4B are schematic views of one embodiment of a plunger 400. The plunger 400 may be made of a metal such as titanium, nickel, aluminum, stainless steel, copper, gold, silver, platinum and alloys thereof or any other biocompatible metal suitable for implantation. In at least some embodiments, the plunger 400 is made of Ti-6Al-4V, or 316L stainless steel. The plunger 400 may also be made of a rigid biocompatible plastic.

The plunger 400 may be, for example, a pin, nail, bolt, dowel, rod, screw or any combination thereof or any other suitable item for engaging and anchoring the lead to the housing. The plunger 400 may engage or couple to the housing by any method such as, for example, tightening, screwing or pushing.

In some embodiments, the plunger 400 is formed of a head 401 and a shaft 402. The head 401 of the plunger 400 may be a smooth surface so that the plunger 400 is simply pushed down into the lead anchor as will be described in greater detail below. The head 401 of the plunger 400 may alternatively have a pattern so that a tool can be used to advance the plunger 400. The pattern of the head 401 may be slotted, Phillips, Frearson, Robertson, hex socket, torx, torq-set or any other suitable pattern. In some embodiments, the head 401 of the plunger 400 is substantially circular and includes one of the patterns described above. In at least some other embodiments, the head 401 of the plunger 400 is itself in a different shape. For example, the head 401 may be in the shape of an ovoid, disk, rectangle, hexagon, square or any other shape useful for advancing the plunger 400.

The shaft 402 of the plunger 400 may also be configured for different embodiments. In some embodiments, the shaft 402 of the plunger 400 is smooth so as to be pushed down into the flexible covering. In at least some other embodiments, the shaft 402 of the plunger 400 has a thread that can be advanced into the flexible covering. Instead of one continuous thread, the shaft 402 of the plunger 400 may also contain one or more separate locking detents 403. (A thread is also a type of locking detent.) The locking detents 403 may be in the form of grooves, passages, ribs or slots disposed on the shaft 402. In some embodiments the locking detents 403 are circumferentially disposed around the shaft 402. The locking detents 403 may also be concentric. In some embodiments, the locking detents 403 are disposed at regular increments along the length of the shaft 402. In at least some other embodiments, the locking detents 403 are disposed at irregular or varying increments. The locking detents 403 are configured to lock the plunger 400 in place within the rigid body. As the plunger 400 is advanced, the locking detents 403 may engage the projecting locking ridges 601 through a series of clicks as the plunger engages the rigid body. The locking detent 403 may also be configured so that it does not allow the plunger 400 to advance beyond a certain point, thereby preventing damage to the lead. The plunger may also have a mechanism (for example, a protruding ridge at, or near, the end of the plunger) that prevents it from being removed from the anchor body.

In at least some embodiments, a mechanism (not shown) is disposed on the plunger 400 for releasing the plunger 400 from the lead anchor assembly. In some embodiments, the mechanism is formed of one or more bosses on the underside of the plunger 400 that could be compressed relative to the housing using a tool so as to unlock the lead from the anchor. The mechanism may also be disposed along the shaft 402 or on the head 401 of the plunger 400. The mechanism may be actuated by compression, twisting, pulling or any other method known in the art.

The plunger 400 is configured and arranged to couple with a housing to secure one or more leads. In some embodiments, the housing is formed of a rigid body and a flexible covering. The rigid body and the flexible covering may be unitary or may be formed separately and then coupled to form the housing. The rigid body and the flexible covering will be described in more detail below with reference to FIGS. 5A and 5B and FIGS. 6A and 6B.

Figure 5A:
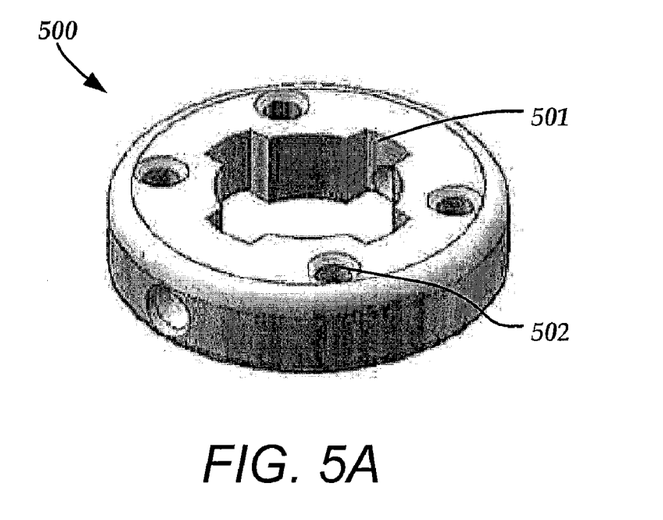
FIG. 5A is a schematic top view of one embodiment of a flexible covering, according to the invention.
Figure 5B:
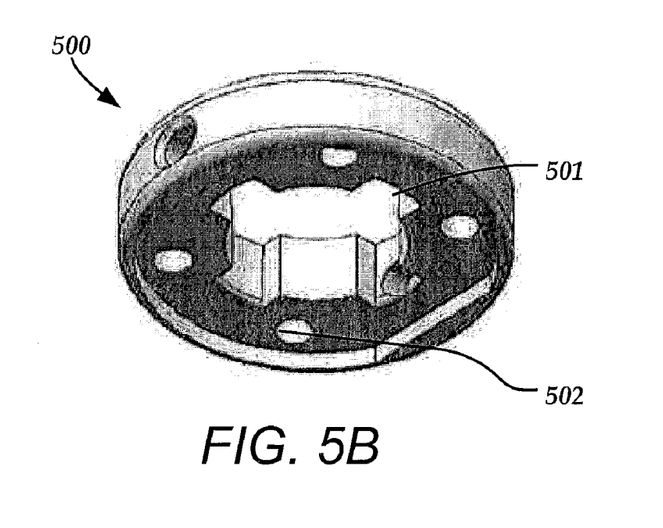
FIG. 5B is a schematic bottom view of the flexible covering of FIG. 5A, according to the invention.

FIGS. 5A and 5B are schematic views of one embodiment of a flexible covering 500. The flexible covering 500 may be made of a plastic, or any flexible polymer, or suitable biocompatible material, including, but not limited to, silicone, polyetheretherketone, polyvinyl chloride, fluoropolymers, polyurethane, polycarbonate, acrylic compounds, thermoplastic polyesters, polypropylene, low-density polyethylenes and other thermoplastic elastomers. In at least some embodiments, the flexible covering 500 is formed from a material dissimilar from that of the plunger 400 to reduce friction and actuation forces.

The optional flexible covering 500 may be disposed around the rigid body. The flexible covering 500 may also be disposed around only a portion of the rigid body, or entirely covering the rigid body and sealing it. In some embodiments, the flexible covering 500 has a substantially disc-like shape as shown in FIGS. 5A and 5B. The substantially disc-like covering may be useful for increasing patient comfort and acceptance of the lead anchor. The flexible covering 500 is not limited to a disc-like shape but may also be square, rectangular, ovoid, or any shape capable of being disposed around the rigid body. In some embodiments where the shape of the flexible covering is polygonal, the edges may be rounded or otherwise smoothed to increase patient comfort.

The flexible covering 500 may also have a plurality of slits 501 for accepting or mating with the rigid body as will be discussed below. In at least some embodiments, the flexible covering 500 further defines at least one suture element 502. The suture element 502 may be a groove, stub, ridge, eyelet, opening or bore or any other suitable arrangement for suturing the flexible covering 500 to the fascia, ligament or other tissue or body structure. The suture element 502 may be positioned anywhere around the circumference of the flexible covering 500. In some embodiments, a plurality of suture elements are disposed on the flexible covering 500.

Figure 6A:
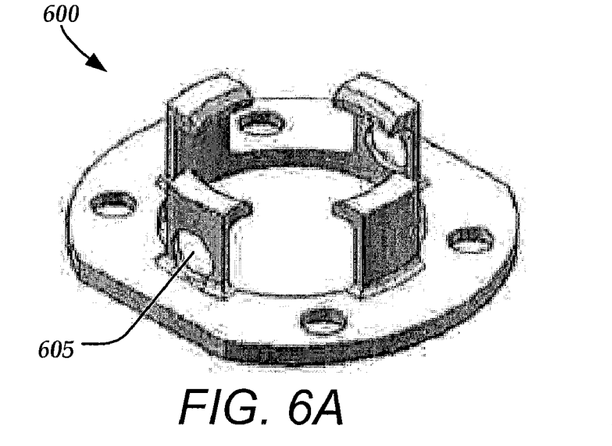
FIG. 6A is a schematic top view of one embodiment of a rigid body, according to the invention.
Figure 6B:
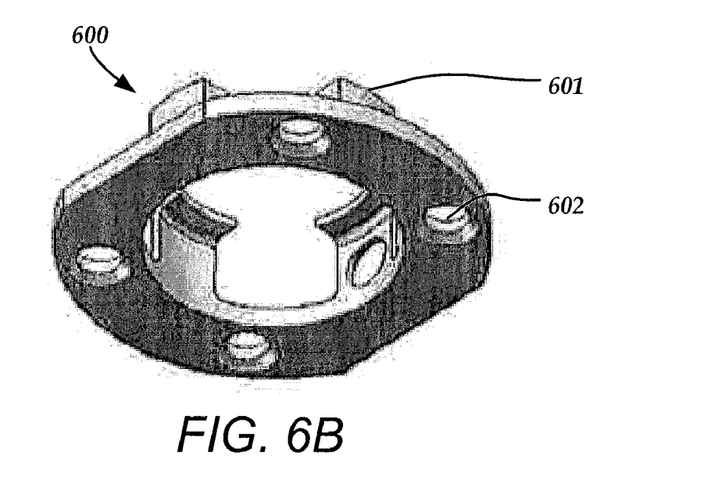
FIG. 6B is a schematic bottom view of the rigid body of FIG. 6A, according to the invention.
Figure 6C:
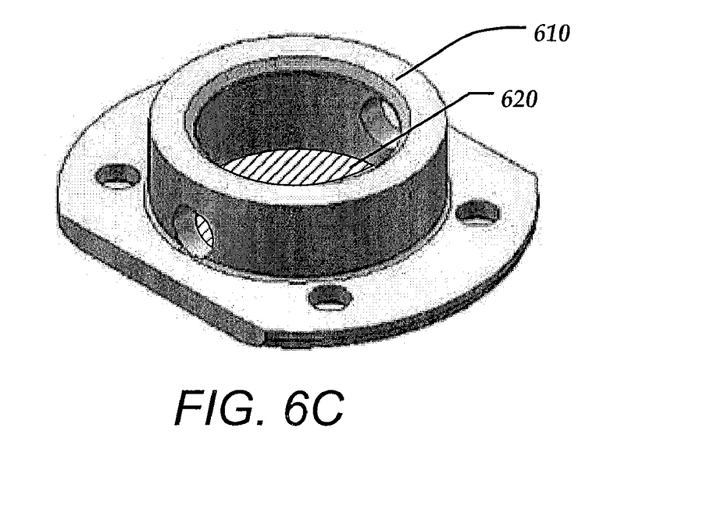
FIG. 6C is a schematic top view of another embodiment of a rigid body, according to the invention.

Turning now to FIGS. 6A, 6B, and 6C, the rigid body will be discussed in more detail. The rigid body 600 may be formed of any of the materials referenced above with respect to the plunger 400 or the flexible covering 500. In some embodiments, the rigid body 600 is made of titanium. In at least some other embodiments, the rigid body is made of polyetheretherketone (PEEK). The rigid body 600 may also be formed of a material dissimilar from the plunger 400 in order to reduce friction and actuation forces.

In some embodiments, the axial cross-section of the rigid body 600 is in a shape substantially similar to or complementary to the flexible covering 500. In some other embodiments, the rigid body 600 may be circular, disk-shaped, square or any shape suitable for anchoring a lead. In some embodiments where the overall cross-sectional shape of the rigid body 600 is polygonal, the edges may be smoothed to increase patient comfort. As seen in FIG. 6C, the bottom of the rigid body 600 may also include a base portion 620 so that the rigid body completely encloses a lead when locked. The base portion 620 may be useful for providing additional compression loading on the lead or for protecting the lead. In some embodiments, the base portion 620 and the rigid body are unitary. In at least some other embodiments, the base portion 620 is a separate member that is snap fit, bonded, welded or coupled to the rigid body 600 in any suitable manner.

As noted above, the rigid body 600 and the flexible covering 500 may be unitary or formed of separate elements. In some embodiments the flexible covering 500 is press-fit onto the rigid body 600. In at least some other embodiments, the flexible covering 500 is bonded or insert-molded to the rigid body 600, or coupled to the rigid body 600 by any other method known in the art.

In some embodiments the rigid body 600 includes one or more projecting locking ridges 601. The projecting locking ridge 601 may be in the form of a tab, a clip, a ridge, a clasp or any other structure capable of fastening the flexible covering 500 to the rigid body 600. In some embodiments, as seen in FIG. 6C, the projecting locking ridge 601 is disposed on an annular rib 610 disposed around the circumference of the rigid body 600. The annular rib 610 may be disposed around the entire circumference of the rigid body 600, or around only a portion of the rigid body 600. The projecting locking ridge 601 is used to couple the housing to the plunger 400 by engaging with the locking detent 403 of the plunger 400. FIGS. 6A and 6B display four projecting locking ridges 601 though any number of projecting locking ridges 601 may be disposed on the rigid body 600. Furthermore, the projecting locking ridges 601 may be disposed on any suitable part of the rigid body 600. In some embodiments, the projecting locking ridge 601 is disposed on the top portion of the rigid body 600. In some other embodiments, the projecting locking ridge 601 is disposed on the sides of the rigid body 600. The projecting locking ridges 601 may also contain openings 605. The openings 605 may be formed of holes, bores, or gaps so that the lead may pass through them. In some embodiments, the rigid body also contains suture elements 602. The suture elements 602 may be similar to or different from those disposed on the flexible covering 500. In some embodiments, the suture elements of the flexible covering 500 are aligned with the suture elements 602 of the rigid body 600.

Furthermore, it may be useful for any or all parts of the lead anchor to be made of a material that is radiopaque, so that it is visible under fluoroscopy or other forms of x-ray diagnosis. In some embodiments, at least one of the rigid body 600 or the flexible covering 500 is radiopaque. In other embodiments, the plunger 400 is radiopaque so as to allow the lead anchor to be readily identified under fluoroscopy or other forms of x-ray diagnosis.

Figure 7A:
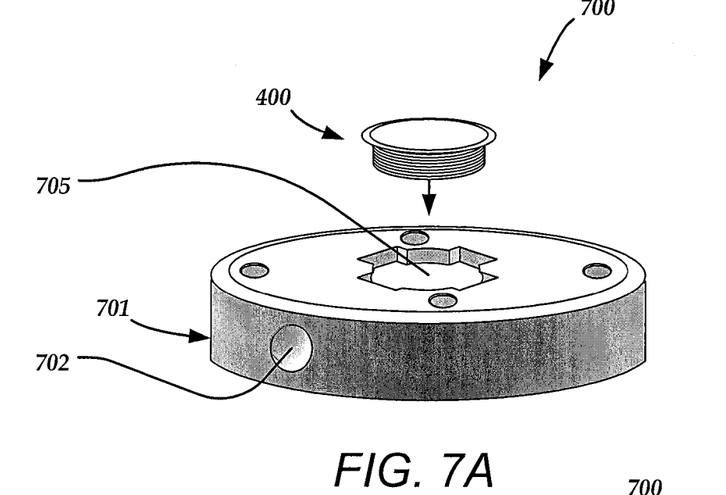
FIG. 7A is a schematic view of one embodiment of a lead anchor, according to the invention.
Figure 7B:
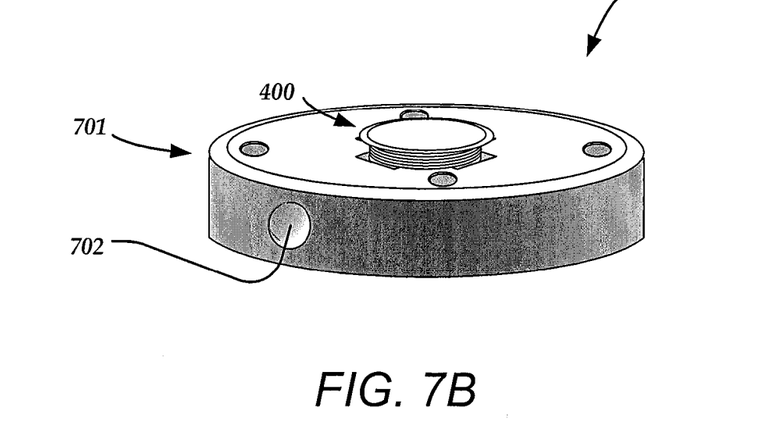
FIG. 7B is a schematic view of the lead anchor of FIG. 7A as the plunger is being inserted into the housing, according to the invention.
Figure 7C:
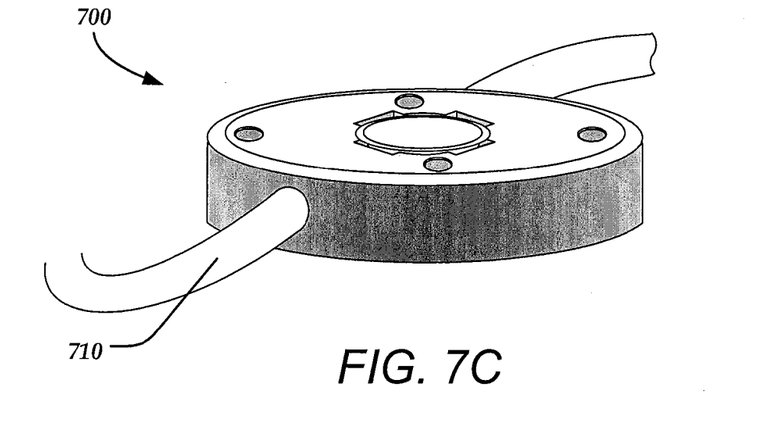
FIG. 7C is a schematic view of the lead anchor of FIG. 7A after a lead has been locked to the lead anchor, according to the invention.

FIGS. 7A-7C are schematic views of one embodiment of a lead anchor. As seen in FIGS. 7A-7C, the housing 701 is configured to receive a lead 710 and a plunger 400. The housing 701 defines a first opening 702 and a second opening (not shown) for accepting the lead 710. In at least some embodiments, a lead lumen is defined within the housing 701. The lead lumen may have a cross-section that is substantially circular as it extends from the first opening 702 to the second opening. It is contemplated that the lead lumen may instead have a cross-section in the shape of a triangle, a square, an ovoid, or any other shape that is large enough to house the lead 710. In some embodiments the lead lumen may be defined so that the lead 710 passes along a straight path through the center of the housing 701. Conversely the lead lumen may be defined so that the lead 710 passes at an angled path through the housing 701. In some embodiments, the lead lumen is defined as a curved path through the housing 701. In some embodiments, the housing 701 contains more than one lead lumen or multiple pairs of openings so that the lead anchor is able to accommodate more than one lead. The lead lumen may be a friction fit with the lead 710 or can be large enough to allow the lead 710 to pass through freely. The lead lumen may be completely defined by the lead anchor or one or more portions of the lead lumen may be open.

The housing 701 further defines a transverse lumen 705 for accepting the plunger 400. The transverse lumen 705 may have a cross-section that is substantially circular. In other embodiments, the housing 701 defines a transverse lumen 705 with a cross-section in the shape of a triangle, a square, an ovoid, or any other shape that is capable of housing the plunger 400. In some embodiments, the transverse lumen 705 is positioned perpendicular to the central axis of the lead lumen. In other embodiments, the transverse lumen 705 may be defined so that the plunger 400 engages a lead 710 within the lead lumen at a 15, 30, or 45 degree angle or any other desirable angle with respect to the central axis of the transverse lumen 705. In at least some embodiments, the transverse lumen 705 merges with the lead lumen but does not extend through it, so that the cross-section of the housing 701 defines a T-shaped bore. In embodiments with multiple lead lumens, the housing 701 may define more than one transverse lumen for accepting a plurality of plungers. Additionally, the housing 701 may define a transverse lumen 705 having a thread, groove, crease, channel, duct or rib for facilitating or accepting the plunger 400. In some embodiments, the transverse lumen 705 has a thread complementary to the thread of the plunger 400.

In some embodiments, the plunger 400 is simply pushed down into the transverse lumen 705. In some other embodiments, a tool such as a clamp or forceps is used to push the plunger 400 into the housing 701. FIG. 7B shows the plunger as it is partially inserted into the housing 701. The lead may be loaded into the lead anchor as illustrated in either FIGS. 7A or 7B. FIG. 7C is a schematic view of the lead anchor of FIG. 7A after a lead 710 has been locked to the housing 701. After a lead 710 has been passed through the first opening 702 of the housing 701 and across the housing 701, a plunger 400 may then be used to secure the lead 710 in place. In some embodiments, the plunger 400 produces a sound, such as a click, when it has been properly engaged and coupled to the housing 701. The plunger 400 and housing 701 may also produce a series of clicks as the plunger 400 is being inserted through the transverse lumen 705. In some other embodiments, the physician is able to feel a snap when the plunger 400 is properly coupled to the housing 701. In at least some embodiments, when the plunger 400 is fully inserted into the housing 701, the head 401 of the plunger 400 is flush or level with the top surface of the housing 701.

Figure 8:
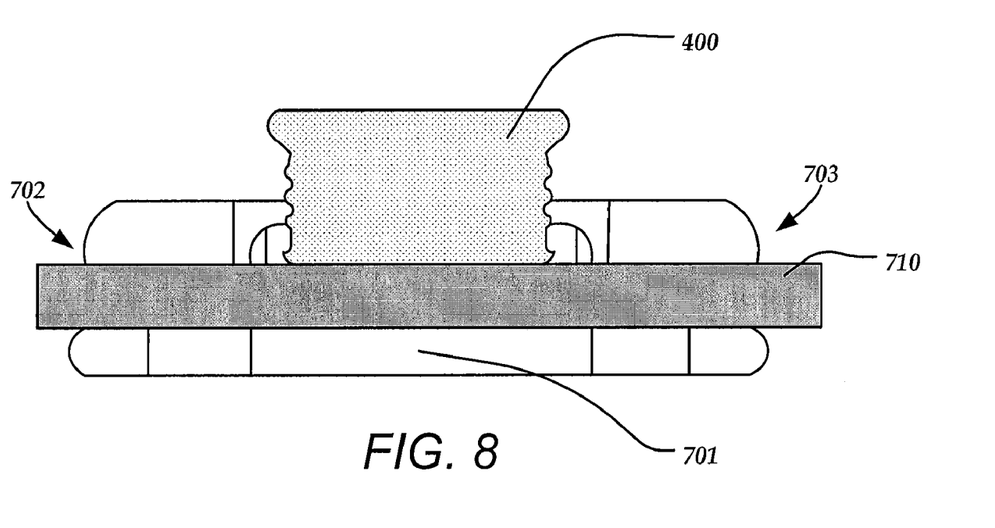
FIG. 8 is a cross-sectional schematic view of one embodiment of a lead anchor before a plunger has been locked to the lead anchor, according to the invention.

FIG. 8 is a schematic cross-sectional view of one embodiment of a lead anchor before a plunger 400 has been locked to the housing 701. As seen in FIG. 8, the lead 710 enters from a first opening 702, travels throughout the length of the housing 701 and exits from a second opening 703. In some embodiments, the lead 710 does not pass straight through the housing 701, but travels upwards, downwards or through any kind of passageway within the housing 701 before exiting from the second opening 703.

Figure 9:
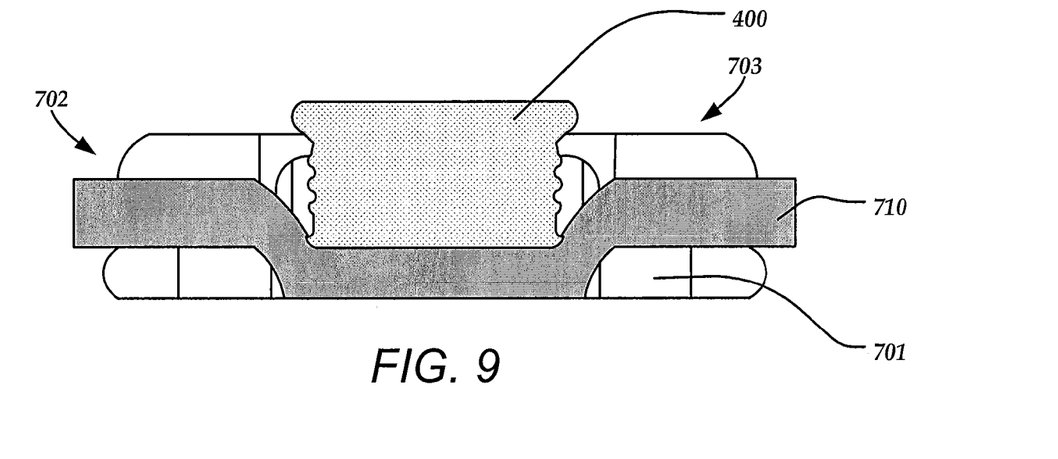
FIG. 9 is a cross-sectional schematic view of one embodiment of a lead anchor after a plunger has been locked to the lead anchor and a lead has been partially deformed, according to the invention.

FIG. 9 is a schematic cross-sectional view of one embodiment of a lead anchor after a plunger 400 has been depressed into the housing 701. In at least some embodiments, the path of the lead 710 is deformed when the plunger 400 is brought into position. In some embodiments, a sleeve or a plate may be disposed around or above the lead to protect it as the plunger 400 is received. The sleeve or plate may be made of any suitable material, such as, for example, a metal such as titanium, nickel, aluminum, stainless steel, copper, gold, silver, platinum and alloys thereof, or a plastic, rubber or polymer such as polyurethane.

Figure 10:
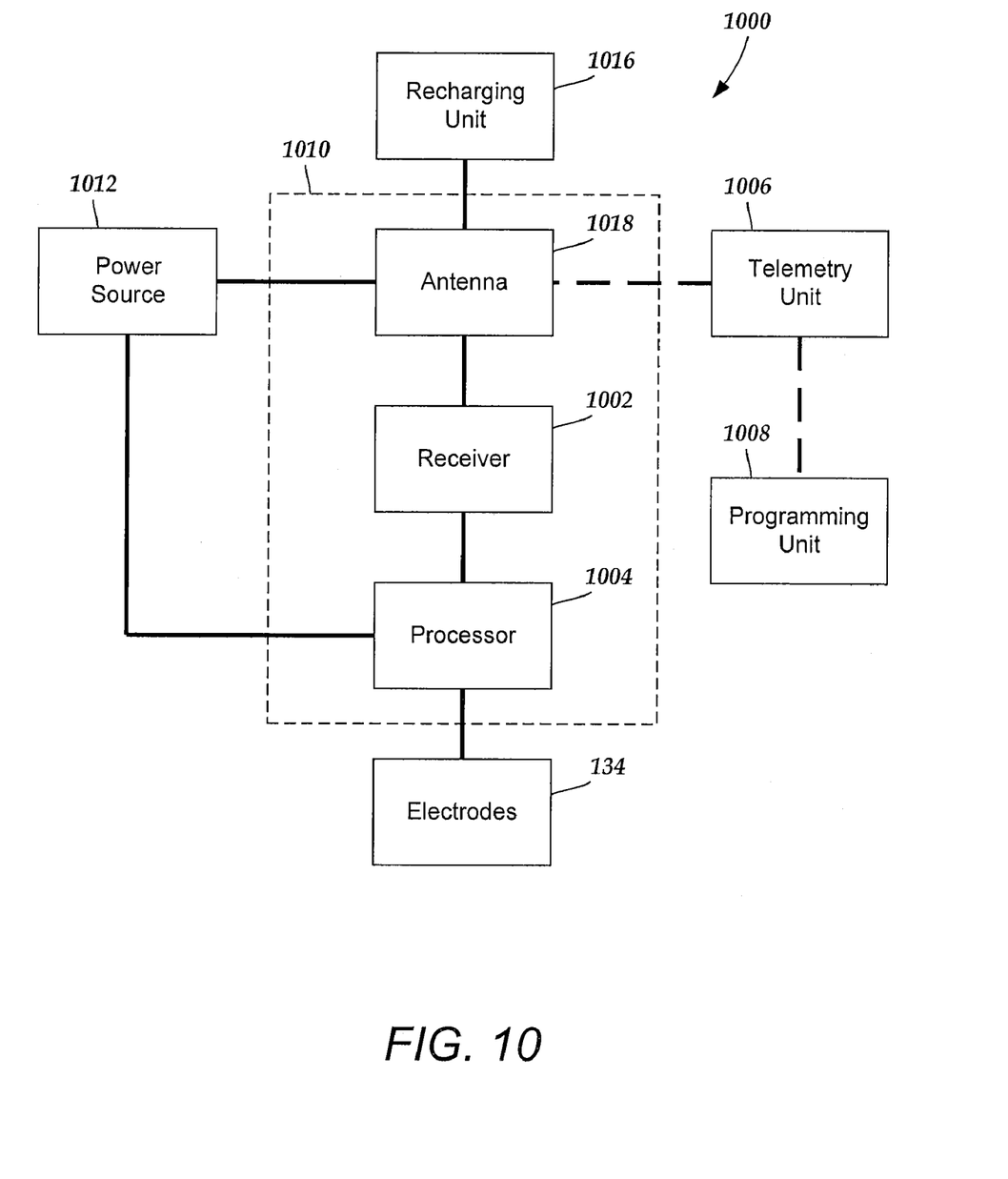
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In at least one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
    a housing comprising a rigid body and a flexible covering disposed over at least a portion of the rigid body, the housing having a top surface, a bottom surface opposite the top surface, and a side surface extending from the top surface to the bottom surface, the housing defining, through the side surface, a first opening and a second opening configured and arranged to receive a lead, wherein boundaries of the first and second openings are circumscribed by the housing, and a lead lumen extending from the first opening to the second opening, the housing further defining a third opening in the top surface of the housing and a transverse lumen which extends from the third opening and intersects with a portion of the lead lumen, the rigid body comprising one or more projecting locking ridges extending into the transverse lumen;
    a plunger comprising a top surface, a bottom surface opposite the top surface, a side surface extending from the top surface to the bottom surface, and one or more locking detents disposed on the side surface, wherein the plunger is configured and arranged for insertion into the transverse lumen and engaging a lead disposed within the lead lumen and, in particular, engaging with a portion of the lead that is disposed within the portion of the lead lumen that intersects with the transverse lumen to press the portion of the lead between the bottom surface of the plunger and the bottom surface of the housing to lock the lead in the lead anchor, wherein the plunger is configured and arranged for locking with the housing by engagement of at least one of the one or more locking ridges of the housing with at least one of the one or more locking detents of the plunger; and
    at least one suture element formed by the flexible covering and configured and arranged for receiving a suture to suture the lead anchor to patient tissue.

2. The lead anchor of claim 1, wherein at least one of the rigid body or the flexible covering is substantially disk-shaped with a circular cross-section.

3. The lead anchor of claim 1, wherein the flexible covering comprises silicone.

4. The lead anchor of claim 3, wherein the rigid body comprises a metal material.

5. The lead anchor of claim 1, wherein the at least one suture element comprises at least one suture opening.

6. The lead anchor of claim 1, wherein the at least one suture element comprises at least one suture ridge.

7. The lead anchor of claim 1, wherein the plunger is configured and arranged to have the top surface of the plunger lie flush with a top surface of the housing when the plunger is fully inserted into the housing.

8. The lead anchor of claim 1, wherein the rigid body and the flexible covering are formed of the same material.

9. The lead anchor of claim 1, wherein the housing and the plunger are formed of dissimilar material.

10. The lead anchor of claim 1, wherein the plunger further comprises a mechanism for releasing the plunger from a locked state within the housing.

11. The lead anchor of claim 1, wherein the flexible covering comprises at least one slit configured and arranged to mate with a portion of the rigid body.

12. The lead anchor of claim 1, wherein at least a portion of one of the housing or the plunger is radiopaque.

13. The lead anchor of claim 1, further comprising a base portion coupled to the housing.

14. An implantable stimulation device, comprising:
    a lead having an electrode array; and
    the lead anchor of claim 1, coupleable to the lead.

15. The implantable stimulation device of claim 14, further comprising a control module coupleable to the lead.

16. The implantable stimulation device of claim 14, wherein the implantable stimulation device is a spinal cord stimulator.

17. A method of implanting an implantable stimulation device, the method comprising:
    implanting a portion of a lead having an electrode array near tissue to be stimulated;
    placing a portion of the lead in a lead anchor, the lead anchor comprising a housing comprising a rigid body and a flexible covering disposed over at least a portion of the rigid body, the housing having a top surface, a bottom surface opposite the top surface, and a side surface extending from the top surface to the bottom surface, the housing defining, through the side surface, a first opening and a second opening configured and arranged to receive a lead, wherein boundaries of the first and second openings are circumscribed by the housing, and a lead lumen extending from the first opening to the second opening, the housing further defining a third openin in the top surface of the housing and a transverse lumen which extends from the third opening and intersects with a portion of the lead lumen, the rigid body comprising one or more projecting locking ridges, the lead anchor further comprising a plunger comprising a top surface, a bottom surface opposite the top surface, a side surface extending from the top surface to the bottom surface, and one or more locking detents disposed thereon, wherein the plunger is configured and arranged for insertion into the transverse lumen and engaging a lead within the lead lumen and, in particular, engaging with a portion of the lead that is disposed within the portion of the lead lumen that intersects with the transverse lumen, wherein the plunger is configured and arranged for locking with the housing by engagement of at least one of the one or more locking ridges of the housing with at least one of the one or more locking detents of the plunger, and at least one suture element formed by the flexible covering and configured and arranged for receiving a suture to suture the lead anchor to patient tissue;

securing the lead to the anchor by pressing the portion of the lead between the bottom surface of the plunger and the bottom surface of the housing; and securing the lead anchor to the surrounding tissue using sutures.

18. The method of claim 17, further comprising implanting a control module and coupling the electrode array to the control module using a lead.

19. The method of claim 17, wherein the step of securing the lead anchor to the surrounding tissue comprises tying a suture to a suture ridge on the exterior member.

20. The implantable lead anchor of claim 1, wherein the plunger is configured and arranged to fit entirely within the transverse lumen of the housing.

* * * * *